US008950344B2

(12) United States Patent
Lewis et al.

(10) Patent No.: US 8,950,344 B2
(45) Date of Patent: Feb. 10, 2015

(54) SURGICAL SUPPORT DEVICE

(71) Applicants: Gerald L. Lewis, McDonough, GA (US); Peggy G. Duke, Atlanta, GA (US)

(72) Inventors: Gerald L. Lewis, McDonough, GA (US); Peggy G. Duke, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/210,898

(22) Filed: Mar. 14, 2014

(65) Prior Publication Data

US 2014/0261099 A1  Sep. 18, 2014

Related U.S. Application Data

(60) Provisional application No. 61/781,305, filed on Mar. 14, 2013.

(51) Int. Cl.
*A47B 3/00* (2006.01)
*A61G 13/10* (2006.01)

(52) U.S. Cl.
CPC ............ *A61G 13/101* (2013.01); *A61G 13/105* (2013.01)
USPC ................................ 108/179; 108/49; 5/507.1

(58) Field of Classification Search
CPC ........................... A47B 23/02; A47B 23/025
USPC ............ 108/3–4, 6–8, 179, 49, 42, 44, 50.01, 108/157.11, 50.02, 166; 211/119.05; 5/600, 5/607, 608, 610, 507.1
See application file for complete search history.

(56) References Cited

U.S. PATENT DOCUMENTS

| 372,288 | A | * | 11/1887 | Bailey | 5/507.1 |
| 798,114 | A | * | 8/1905 | Rosentahl | 482/130 |
| 975,755 | A | * | 11/1910 | Eyles | 297/145 |
| 1,134,720 | A | * | 4/1915 | Bradley | 5/622 |
| 2,119,325 | A | * | 5/1938 | Goodhart | 602/16 |
| 2,628,803 | A | * | 2/1953 | Krewson | 248/124.2 |
| 2,696,963 | A | * | 12/1954 | Shepherd | 248/229.15 |
| 3,020,909 | A | * | 2/1962 | Stevens | 602/39 |
| 3,476,256 | A | * | 11/1969 | Anderson | 211/119.005 |
| 3,623,616 | A | * | 11/1971 | Engelsher | 211/119.005 |
| 3,859,993 | A | * | 1/1975 | Bitner | 128/847 |
| 4,113,218 | A | * | 9/1978 | Linder | 248/291.1 |
| 4,557,453 | A | * | 12/1985 | McCloskey | 248/287.1 |
| 4,686,727 | A | * | 8/1987 | Wilkinson | 5/503.1 |
| 4,747,172 | A | * | 5/1988 | Hohol et al. | 5/507.1 |

(Continued)

OTHER PUBLICATIONS

F. Cole (1951), "Improved Anesthesia Screen", JAMA, 147(4): 318.

(Continued)

*Primary Examiner* — Hanh V Tran
(74) *Attorney, Agent, or Firm* — Emory Patent Group

(57) ABSTRACT

A surgical support device can provide members for attaching various medical accessories in a safe, stable and secure manner. The surgical support device can also configured to isolate the sterile field from the non-sterile field to better enhance infectious control measures. The surgical support device may include at least two side supports configured to extend vertically from the side rail, each side support including a support member; a transverse member disposed between the two side supports; at least two support members; at least one platform configured to be pivotable between the transverse member and the support member; and at least one accessory arm extending from at least one of the at least two side supports and configured to pivot around the at least one of the at least two side supports; and a plurality of accessory attachment members configured to secure and/or support one or more accessories.

19 Claims, 8 Drawing Sheets

(56) References Cited

U.S. PATENT DOCUMENTS

| | | | |
|---|---|---|---|
| 5,152,486 A * | 10/1992 | Kabanek et al. | 248/201 |
| 5,333,929 A * | 8/1994 | Slagerman | 297/155 |
| 5,357,873 A * | 10/1994 | Hilton | 108/50.01 |
| 5,362,021 A * | 11/1994 | Phillips | 248/276.1 |
| 5,375,276 A * | 12/1994 | Nelson et al. | 5/620 |
| 5,437,493 A * | 8/1995 | Weisleder | 297/150 |
| 5,816,648 A * | 10/1998 | Baccili et al. | 297/159.1 |
| 5,927,214 A * | 7/1999 | Schwartz et al. | 108/128 |
| 5,964,165 A * | 10/1999 | Schmidt et al. | 108/158.11 |
| 6,298,507 B1 * | 10/2001 | Clyburn | 5/623 |
| 6,314,891 B1 * | 11/2001 | Larson | 108/44 |
| 6,471,167 B1 * | 10/2002 | Myers et al. | 248/177.1 |
| 6,702,373 B2 * | 3/2004 | Rossko | 297/173 |
| 6,994,034 B2 * | 2/2006 | Chang | 108/115 |
| 7,216,929 B2 * | 5/2007 | Lang et al. | 297/155 |
| 7,448,099 B2 * | 11/2008 | Abernathie | 5/507.1 |
| 7,523,514 B2 * | 4/2009 | Salt et al. | 5/503.1 |
| 2003/0101512 A1 * | 6/2003 | Jensen et al. | 5/503.1 |
| 2009/0260159 A1 * | 10/2009 | Buchanan | 5/617 |
| 2011/0083274 A1 * | 4/2011 | Newkirk et al. | 5/624 |

OTHER PUBLICATIONS

Access II, Adjustable Anesthesia Screen [online]. Pemco Incorporated [retrieved on Mar. 12, 2013]. Retrieved from the Internet: <URL:http://www.pemcomed.com/pdf/Screen%20RevA%204_21_2011-2_AccessII.pdf>.

* cited by examiner

SURGICAL SUPPORT DEVICE

CROSS REFERENCE TO RELATED APPLICATION

This application claims priority to Provisional Application Ser. No. 61/781,305 filed Mar. 14, 2013, which is hereby incorporated by reference in its entirety.

BACKGROUND

During surgery, draping often occurs at the head of a patient to create a sterile barrier separating the surgical field from the anesthetist's access to the patient. Typically, on one side of the sterile barrier, an assortment of invasive tubes, lines, catheters, wires and other devices are attached to the patient during the course of the surgery. Generally, these tubes, lines, catheters, wires, and other device come from different parts of the patient's body and connect to monitors, screens, drip lines, injection ports, and other devices on the other side of the barrier near the head of the patient. Many of these monitors, screens, drip lines, injection ports, and other devices are under the anesthesiologist's control during the course of surgery. Thus, this area can be easily cluttered.

Additionally, the surgical field near the barrier can be further cluttered by placement of surgical instruments on the drape. This cluttering and disorganization can apply undue pressure to the patient and to the monitoring lines, and can result in possible injury to the patient (e.g., from a falling instrument). Thus, the clutter and disorganization on both sides of the barrier can also be harmful to the patient.

U.S. Pat. No. 3,623,616 discloses an anesthesia screen. U.S. Pat. No. 4,113,218 discloses an adjustable frame assembly for supporting a surgical tray. U.S. Patent Publication No. 2003/0101512 discloses an adjustable shelf/tray and anesthesia screen. Pemco Medical sells an anesthesia shield with an adjustable screen (Access II).

SUMMARY

Thus, there is a need for a surgical support device that is configured to create a sterile barrier, while organizing and without interfering with the anesthesiologist and surgical fields of view.

The disclosure relates to a surgical support device that is configured to organize the surgical field on both sides of the barrier without interfering with the visibility of or access to the patient (e.g., head, neck and face).

In some embodiments, the disclosure relates to a surgical support device configured to be disposed on a side rail of a surgical table. The surgical support device can be configured to be removably attached to the side rail so that the surgical support device is above the patient (e.g., surrounds the head region of the patient). In some embodiments, the device may include at least two side supports configured to extend vertically from the side rail, each side support including a support member; a transverse member disposed between the two side supports; at least one platform configured to be pivotable between a first position and a second position; and at least one accessory attachment member configured to secure and/or support one or more accessories. In some embodiments, the at least one platform may be disposed substantially adjacent to the transverse member in the first position and the at least one platform may be disposed substantially adjacent to the support member in the second position.

In some embodiments, the device may include at least two connectors, each connector disposed at an end of the side support and configured to at least partially surround the side rail and fixedly dispose the device to the surgical table. In some embodiments, the device may include at least one accessory arm extending from the side support and being configured to pivot around one of the at least side supports; and a locking mechanism configured to releasably lock the accessory arm in position.

In some embodiments, the device may further include a plurality of accessory attachment members. In some embodiments, one or more of the following may include at least one accessory attachment member: the accessory arm, at least one of the at least two side supports, the transverse member, and at least one of the at least two support members. In some embodiments, each accessory arm may include at least two accessory attachment members.

In some embodiments the device may be configured to move between an expanded position and a collapsed position. In some embodiments, the at least two side supports, the at least one accessory arm and/or the at least one platform may be configured to be collapsed so as to be disposed substantially adjacent to the transverse member.

In some embodiments, each side support may include two legs, one of the legs of each side support being longer than another leg of the side support. In some embodiments, the two side supports may include a first side support and a second side support.

In some embodiments, the surgical support device may include at least two side supports configured to extend vertically from the side rail, each of the side supports including a set of legs; a transverse member disposed between the at least two side supports and a support member disposed perpendicular to and between each set of legs; at least one platform configured to be pivotable between the transverse member and the support member; and at least one accessory arm extending from the at least one of the at least two side supports and configured to pivot around the at least one of the at least two side supports; and a plurality of accessory attachment members configured to secure and/or support one or more accessories. In some embodiments, the plurality of accessory attachment members may be disposed on at least one of the following: the at least one accessory arm, at least one of the at least two side supports, the transverse member, and the support member.

In some embodiments, the surgical support device may include at least two side supports configured to extend vertically from the side rail, each side support including a support member; a transverse member disposed between the at least two side supports; at least one platform configured to be pivotable between the transverse member and the support member; at least one accessory arm extending from the at least one of the at least two side supports and configured to pivot around one of the at least two side supports; and a plurality of accessory attachment members configured to secure and/or support one or more accessories. In some embodiments, the at least one accessory arm, at least one of the at least two side supports, the transverse member, and/or the support member may include at least one accessory attachment member. In some embodiments, the device may be configured to move between an expanded position and a collapsed position. In some embodiments, when the device is in the collapsed position, the at least two side supports, the at least one platform, and/or the at least one accessory arm may be disposed substantially parallel to the transverse member.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
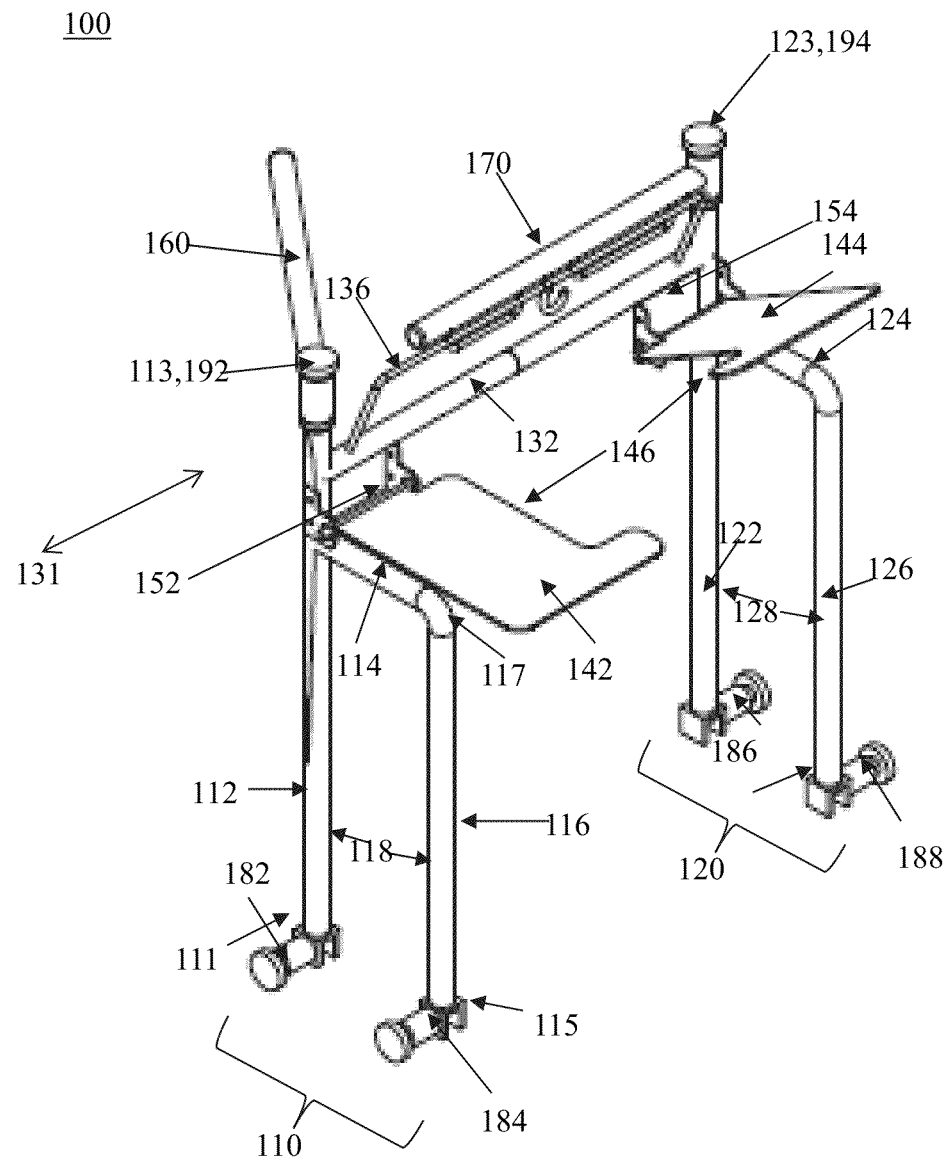
FIG. 1 is a perspective view of a surgical support device according to embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The surgical support devices according to embodiments can address potentially problematic obstruction and disorganization of the anesthesiologist and surgical fields of view that can be associated with conventional anesthetic screens. The surgical support devices can also provide members for attaching various medical equipment, supply hoses, etc. in a safe, stable and secure manner. The surgical support devices can also be configured to isolate the sterile field from the non-sterile field to better enhance infectious control measures. The surgical support devices can be used with a surgical drape/sheet, while serving as a conduit to supply the anesthetist a direct and unobstructed route to the patient's upper body region (head and neck region). The surgical support devices can also be constructed to allow for easy positioning and transporting on a surgical table, as well as easy storage when not in use. For example, the surgical support devices can be configured to be at least partially collapsible.

FIGS. 1 through 8 show a surgical support device according to embodiments. FIGS. 1 through 4 show a surgical support device 100 according to embodiments. FIGS. 5-8 show different views of device 500, which is an example of a prototype of the device 100.

As shown in FIG. 1, the surgical support device 100 may include at least two opposing side supports 110 and 120. The side supports may be configured to extend vertically from each of the side rails of a surgical table so that the device bridges the surgical table. The patient may be disposed between the side supports. One of the ends may be configured to be substantially adjacent to the side rails of a surgical table.

In some embodiments, each of the side supports may include one or more legs. In some embodiments, one or more of the side supports may include a set of legs. For example, as shown in FIG. 100, the device 100 may include two sets of opposing legs. In some embodiments, the first side support 110 may include a set of legs (a (first) leg 112 and a (second) leg 116) and an opposing second side support 120 may include a set of legs (a (third) leg 122 and a (fourth) leg 126). In some embodiments, the leg 112 and the leg 122 may be configured to be disposed closest to an edge of the side rail (e.g., closest to the anesthesiologist's field).

In some embodiments, the leg 112 may include a first end 111, an opposing second end 113, and a length therebetween; the leg 116 may include a first end 115, an opposing second end 117 and a length therebetween; the leg 122 may include a first end 121, an opposing second end 123, and a length therebetween; and the leg 126 may include a first end 125, an opposing second end 127 and a length therebetween. The first ends may be configured to be substantially adjacent to the side rails of a surgical table.

In some embodiments, the side supports may be substantially similar. In other embodiments, the side supports may be different. For example, the side supports may have different lengths. For example, the legs of each side support may have the same or different shape.

In some embodiment, the length of the legs of each side support may be substantially the same. In other embodiments, the length of the corresponding leg may be substantially different. For example, as shown in FIG. 1, in each set, one of the legs may be longer than the other. The leg 112 may be longer than the leg 116 and the leg 122 may be longer than the leg 126. In other embodiments, the legs may be of the same length.

In some embodiments, the side supports and/or legs may be substantially a solid frame (i.e., the frame may be hollow with no accessible openings or apertures disposed along its length). In other embodiments, the side supports and/or legs may include at least one accessible opening or aperture disposed along its length. One or more of these openings may be configured to assist an operator with handling the device (e.g., a handle), an accessory attachment member (discussed in more detail below), other uses, or a combination thereof.

The side supports and/or legs may have any shape. In some embodiments, the legs may have a substantially circular shape. In other embodiments, the legs may have substantially rectangular shape or elongated shape.

In some embodiments, at least one side support may be configured to be releasably, fixedly disposed to a side rail of a surgical table. In some embodiments, at least one of the side supports may include a connector configured to releasably, fix the device to the side rail. In some embodiments, each of the legs may include a connector. As shown in FIGS. 1-4, the legs 112, 116, 122, and 126, may include connectors 182, 184,

186, and 188, respectively. The connectors 182, 184, 186, and 188 may be disposed on ends 111, 115, 121 and 125, respectively.

The connectors may be the same/or different. FIG. 2B shows an example of an enlarged view of one of the connectors (connector 186). The connector 200 may include a clamp 202 configured to disposed above and at least partially surround the side round. In some embodiments, the connector may include a locking mechanism 204 configured to releasably fix the clamp to the rail. The locking mechanism 204 may include but is not limited to a knob mechanism. The locking mechanism 204 may be configured to be disposed perpendicular to the side rail. In some embodiments, the connector 200 may include a pivoting internal cap structured to secure the support device to the side rails without causing damage.

In some embodiments, the device 100 may include at least one support member configured to provide a support surface. The support member may be configured to support a platform, for example, for medical instruments, operation personnel during surgery (e.g., support personnel's arm during a procedure), as well as other support in the surgical field. In some embodiments, the at least one side support may each include a support member.

In some embodiments, the support members may have the same and/or different shape. In some embodiments, the support members may have a substantially circular shape. In other embodiments, the support members may have a substantially rectangular shape.

In some embodiments, the device 100 may include a first support member 114 and an opposing second support member 124. The support members may be disposed perpendicular to the length of the side supports and near the second end of the side supports (the end opposing the side rails) (when the device is in an open position). In some embodiments, the support members may be disposed at the same height with respect to the side supports. In other embodiments, the support members may be disposed at different lengths with respect to the side supports. In some embodiments, the supports members may be disposed at the second end of one of the side supports and at a position along the length of the other side support.

In some embodiments, the first support member 114 may extend substantially perpendicularly between the legs 112 and 116, and the second support member 124 may extend substantially perpendicularly between the legs 122 and 126. In some embodiments, the support member may be rigidly disposed between each set of legs.

In some embodiments, the device 100 may include at least one opening disposed below the support member and within the side support, below the support member and between the legs, within at least one leg, or a combination thereof. For example, the device 100 may include opening 118 and opening 128. In some embodiments, the openings may have any size, shape, and position. In some embodiments, the opening may be smaller. In some embodiments, the opening may be disposed within each side support. For example, the legs of each side support may not be separated and the side support may be substantially solid.

In some embodiments, the device 100 may include a transverse member 132 disposed between the side supports 110 and 120. The transverse member 132 may be disposed between the leg 112 and the leg 122. The transverse member 132 may be configured to be disposed adjacent to an end of the bed closest to the anesthesiologist field.

In some embodiments, the transverse member 132 may be rigidly disposed between the side supports 110 and 120. In other embodiments, the transverse member 132 may be configured to be collapsed or folded, for example, along axis 131. In some embodiments, at least one of side supports 110 and 120 may be configured to pivot with respect to the transverse member 132. For example, the side supports 110 and 120 may be configured to fold or collapse with respect to the transverse member. In some embodiments, at least one of the side supports 110 and 120 may be connected to the transverse member 132 with a pivot member (133 and 135). The pivot member may include but is not limited to a hinge-like mechanism. In some embodiments, in the collapsed state or position, the side supports 110 and 120 may be disposed substantially parallel to the transverse member.

In some embodiments, the device may include at least one pivotable support platform. The support platform may be configured to provide stability and support for medical instruments, operation personnel during surgery (e.g., support personnel's arm during a procedure), as well as other support throughout the surgery. The support platform may be configured to be disposed substantially along the length of the support member(s). In some embodiments, the support platform may be longer than the length of the support member(s). In other embodiments, the support platform may be shorter than the length of the support member(s).

In some embodiments, the device may include an opening configured to provide the patient (e.g., head and upper torso area). In some embodiments, the support platform may include an opening configured to provide access to the patient (head) (e.g., observation area). In some embodiments, the support platform may be substantially disposed between the side supports. For example, the support platform may have a rectangular shape that extends substantially along the length of the transverse member (e.g., between the side supports) and rests on the respective support members. The support platform may include an opening for access to the patient, for example, having a rectangular or circular shape disposed within the platform (e.g., disposed substantially in the center).

In other embodiments, the device may include at least one support platform that merely extends along a portion of the length of the transverse member so as to leave an opening configured to provide access to the patient. In some embodiments, the device may include one support platform. In other embodiments, the device may include two support platforms. The two support platforms may be separated so as to provide an opening for access to the patient. In other embodiments, the device may include more than two support platforms.

In some embodiments, the two support platforms may be configured to move independently. This can allow the operation personnel greater access to the patient's upper torso without removing the support device from the surgical table. In other embodiments, the two support platforms may be configured to be collectively.

The at least one support platform may be configured to pivot between the transverse member (an open or first position) and the support member (a closed or second position). In this way, the support platform can be disposed substantially adjacent to the transverse member in the open or first position, for example, when the device is collapsed and/or when operation personnel want to access the patient. In the first or closed position, the support platform may be used as stability and support for medical instruments, operation personnel during surgery (e.g., support personnel's arm during a procedure), as well as other support throughout the surgery.

In some embodiments, the device may include at least one securing member configured to maintain and/or secure the position of at least one support platform. In some embodiments, the secure member may be configured to secure the at least one platform adjacent to the transverse member and/or support member. In some embodiments, the at least one platform may be disposed directly adjacent to and/or substantially abut the transverse member and/or support member.

Figure 2A:
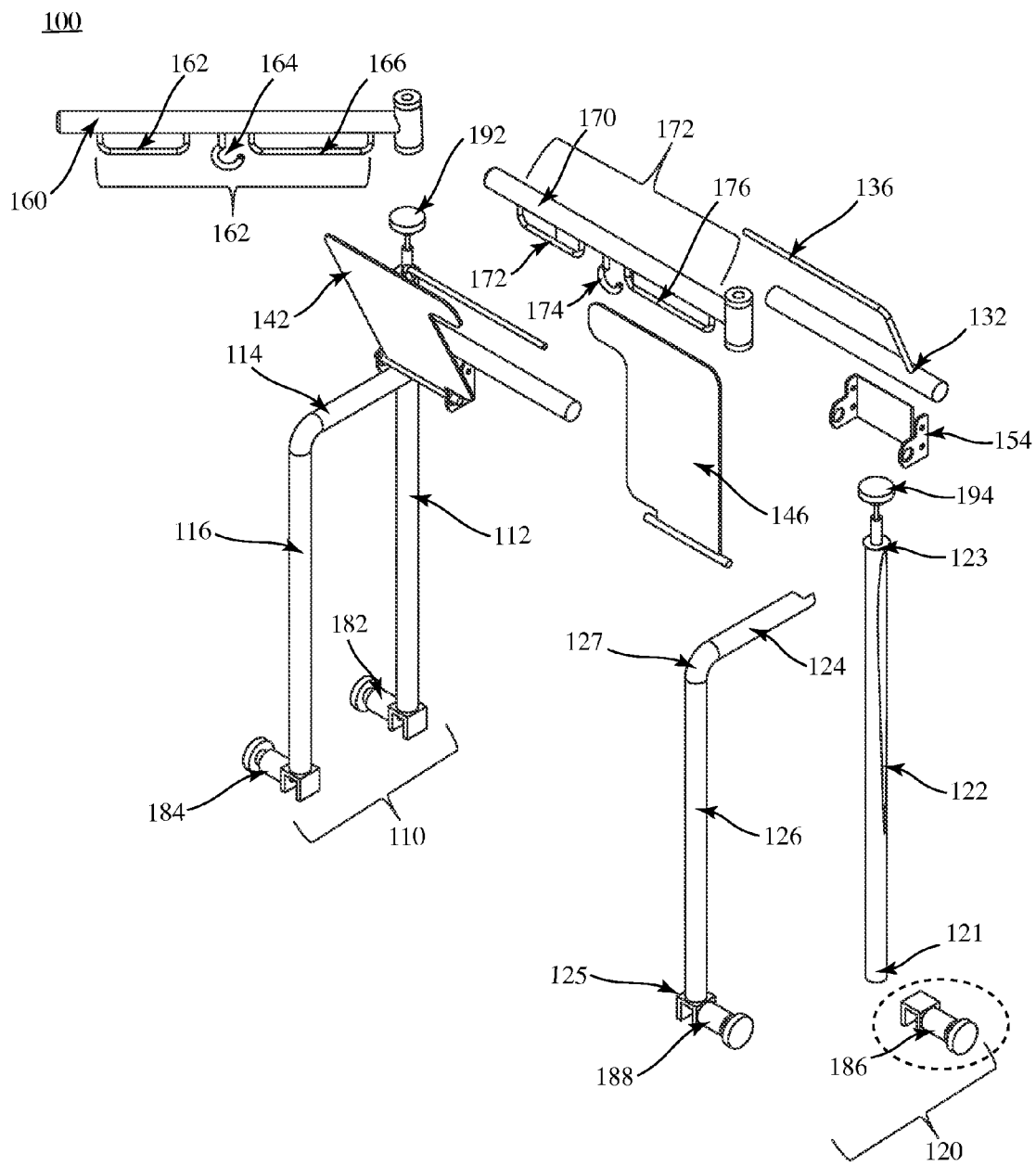
FIG. 2A is an exploded view of the surgical support device of FIG. 1.
Figure 2B:
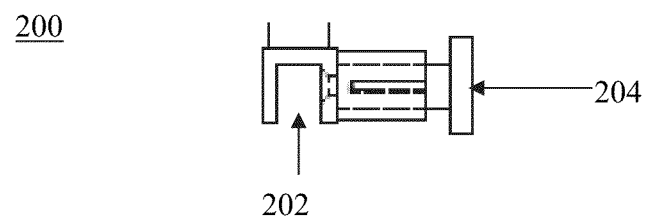
FIG. 2B is a partial enlarged view of the surgical support device of FIG. 1.
Figure 3:
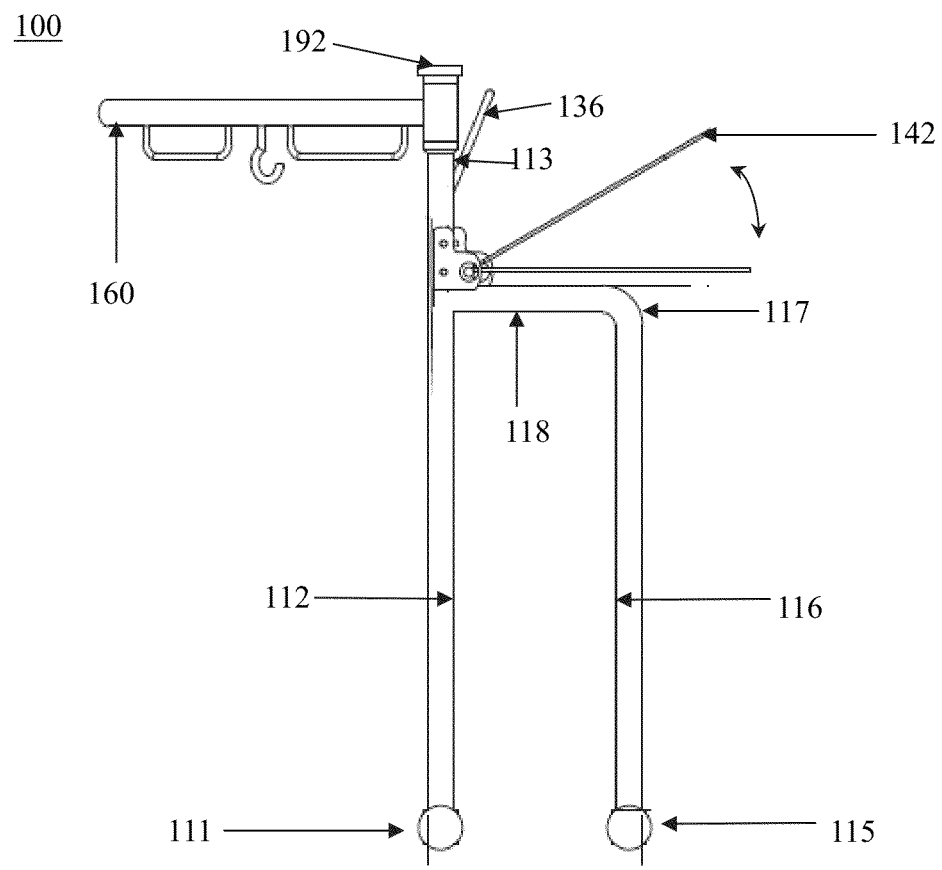
FIG. 3 is a side view of the surgical support device of FIG. 1.

As shown in FIGS. 1-3, the device 100 may include a (first) support platform 142 and a (second) support platform 144. The platforms 142 and 144 may be separated by an opening 146 configured to provide access to the patient. The first support platform 142 may be configured to pivot with respect to the transverse member 132 and to be disposed on support member 114 (in expanded state or position), and the second support platform 144 may be configured to pivot with respect to the transverse member 132 and to be disposed on support member 124 (in expanded state or position).

In some embodiments, the device may include a pivoting mechanism for each support platform. The pivoting mechanism may include but is not limited to a bracket in which the support platform may pivot (e.g., like a rod). As shown in FIGS. 1-3, the device 100 may include pivoting mechanisms 152 and 154 for platforms 142 and 144, respectively. The pivoting mechanisms 152 and 154 may be disposed between the transverse member and the respective support members 114 and 124, respectively.

In some embodiments, the support platforms may have any shape or structure. The support platforms may be the same or different. For example, at least one of the support platforms may each be a flat, level surface. In other embodiments, at least one of the support platforms may have a different structure. For example, one of the support platforms may include a structure specific to an accessory or operating support device, such as an ergonomic support for the operation personnel (e.g., an arm rest device to provide support to the operation personnel).

Figure 5:
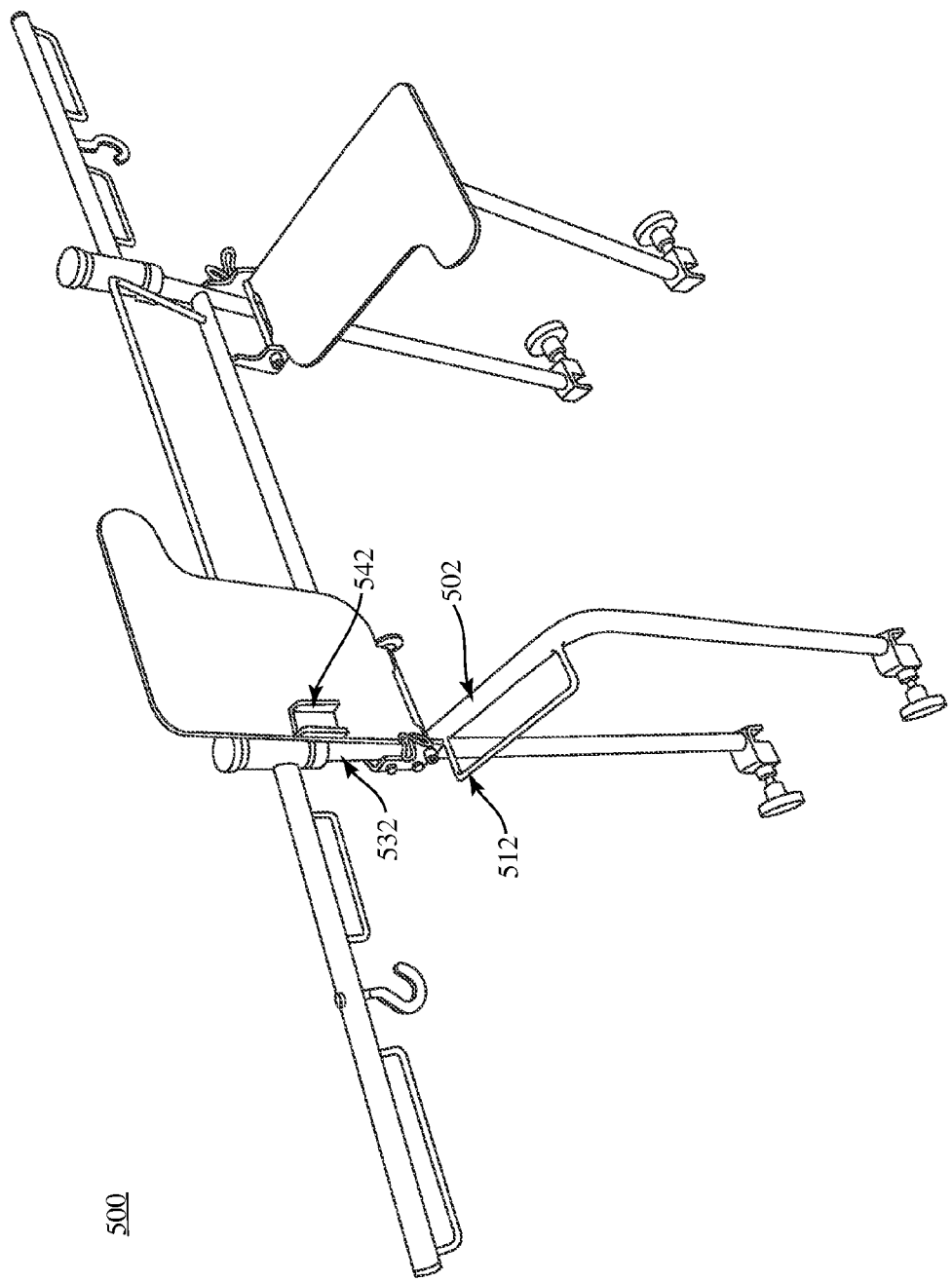
FIG. 5 shows a perspective view of a prototype of a surgical support device according to embodiments.
Figure 6:
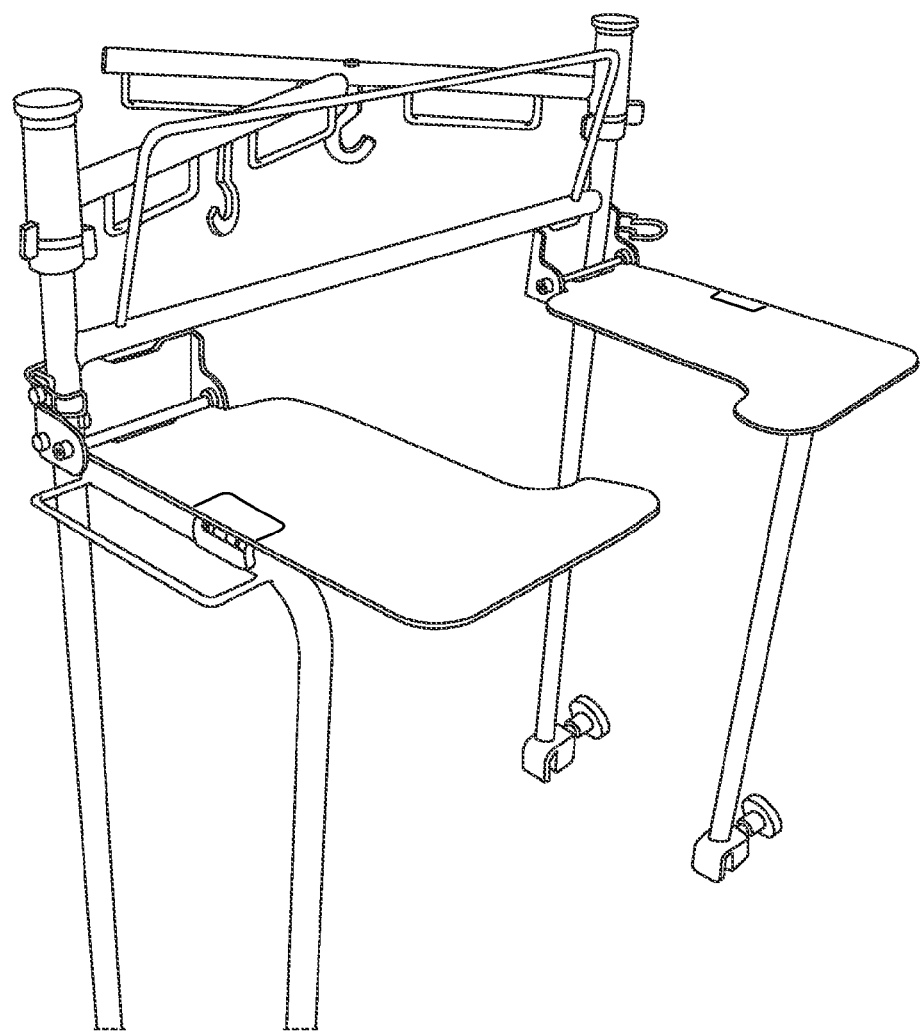
FIG. 6 shows another perspective view of a partially collapsed prototype of the surgical support device of FIG. 5.
Figure 7:
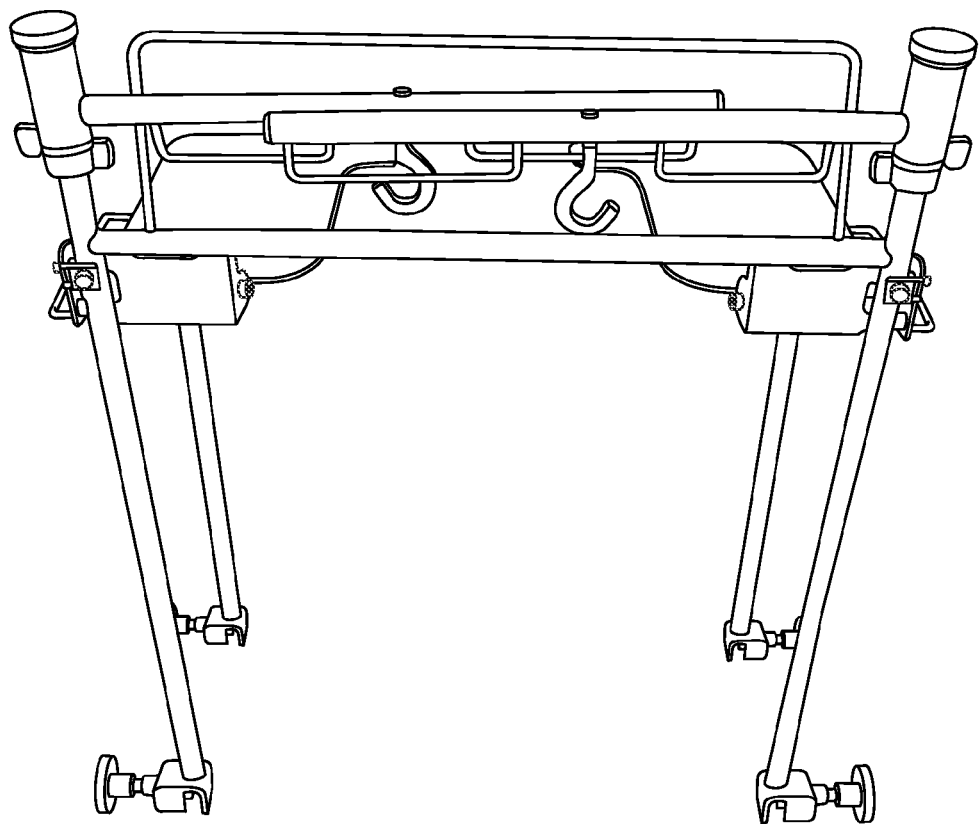
FIG. 7 shows a rear view of a partially collapsed prototype of the surgical support device of FIG. 5.
Figure 8:
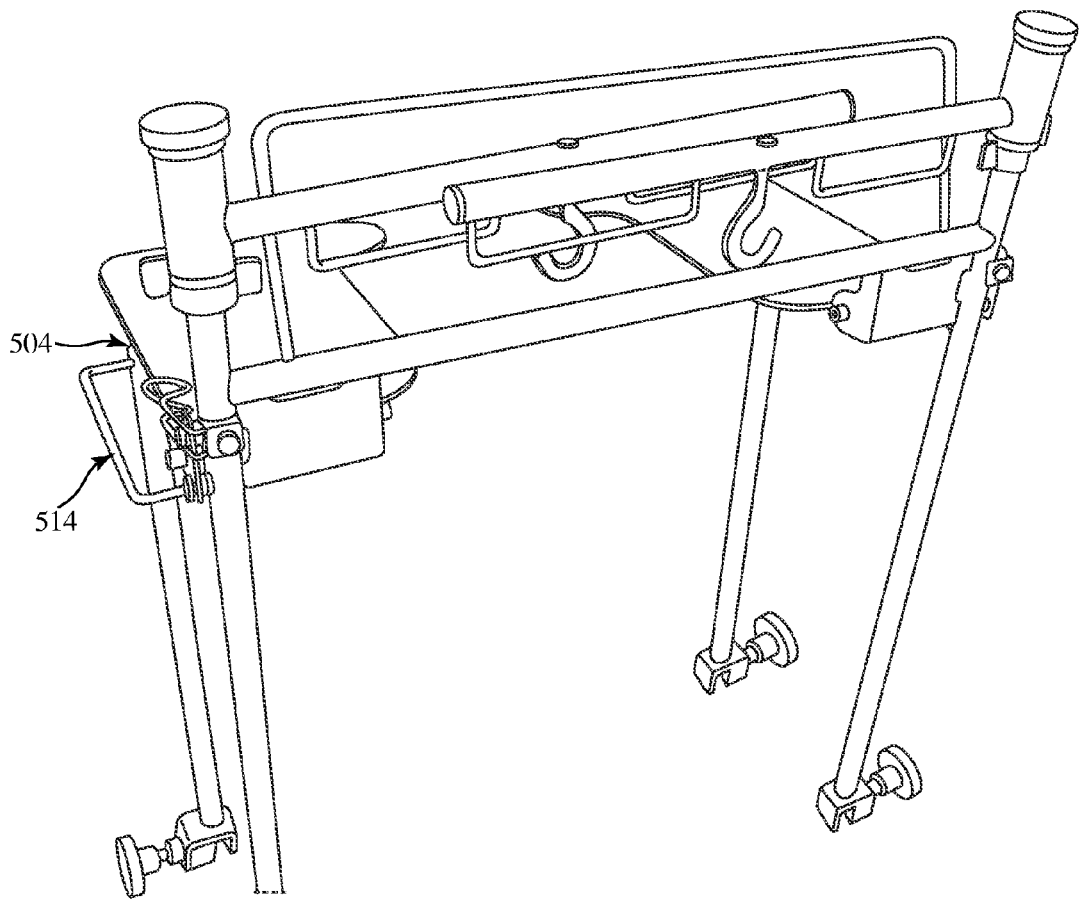
FIG. 8 shows a rear perspective view of FIG. 7.

As shown in FIG. 5, the device may include at least one securing member configured to maintain and/or secure the position of at least one support platform with respect to the support member and/or transverse member. In some embodiments, the device may include at least one securing member 532 disposed on one of the legs and be configured to secure the at least one support platform substantially parallel to and adjacent to the transverse member (e.g., in an open or first position). In some embodiments, the at least one securing member 532 may include but is not limited to a spring clip assembly. In some embodiments, the at least one securing member 532 may be automatic. For example, when the support platform is lifted and moved towards the transverse member, the securing member 532 may be configured to automatically latch.

In some embodiments, the device may include a securing member 542 disposed on a side of the support platform configured to maintain and/or secure the support platform with respect to the support member (e.g., in the second or closed position). The securing member 542 may include but is not limited to a clamp-type device.

In some embodiments, the device may include at least one securing member for each support platform. In some embodiments wherein the device may include at least two support platforms, the device may include at least one securing member for each support platform.

In some embodiments, the device may include at least one support arm configured to secure the drape/sheet. In some embodiments, the support arm(s) may be configured to be fixedly disposed with respect to the side support. In other embodiments, the support arm(s) may be configured to be adjustable with respect to the side support. The support arm(s) may be configured to rotate about a side support (between the side support and the transverse member). This provides flexibility in disposing the arms throughout the surgery, as well as during moving and storage. The support arm(s) may be configured to be collapsed (or in a collapsed position) so as to be parallel to the transverse member. (e.g., folded against and/or abut the transverse member).

In some embodiments, the device 100 may include a (first) support arm 160 and a (second) support arm 170. The support arm 160 may be disposed at the end 113 of the side support 110 and the support arm 170 may be disposed at the end 123 of the side support 120.

In some embodiments, the support arm(s) may have a length that substantially corresponds to the length of the transverse member. In other embodiments, the support arm(s) may have a length that corresponds to at least a portion of the length the transverse member. In some embodiments, the support arm(s) may have a length that is longer than the length of the transverse member.

In some embodiments, the support arm(s) may have the same length. In other embodiments, the support arm(s) may have a different length. The support arm(s) may have a different shape and/or same shape.

In some embodiments, the device may include a locking mechanism configured to temporarily lock the position of each support arm. The locking mechanism may be disposed at an end of a side support and/or leg around which the support arm rotates or pivots. In some embodiments, the device may include but is not limited to a knob. As shown in the figures, the device 100 may include a locking mechanism 192 disposed at end 113 for support arm 160 and a locking mechanism 194 disposed at end 123 for support arm 170.

In some embodiments, the device may include one or more accessory attachment members configured to secure and/or support one or more accessories used throughout surgery, and thereby organize the anesthesiologist and surgical fields. The accessories may include but are not limited to tubes, lines, catheters, wires, and other devices that are used during a surgical procedure, as well as their respective connections (e.g., monitors, screens, drip lines (e.g., IV bags), pressure lines, injection ports, etc.) for monitoring by anesthesiologist, as well as other operation personnel, among others, or a combination thereof. The accessory attachment member may also be used to support and secure a medical drape.

The accessory attachment member(s) may have the same and/or different shape, configuration, size, etc. In some embodiments, the accessory attachment member may be a surface and/or opening configured to support an accessory. For example, the accessory attachment member may include but is not limited to a hook, rod, or hanger-like shape. The hook may be an open hook or a closed hook. The accessory attachment member may be configured to securely support an accessory by itself, with support of another device (e.g., a clip), or a combination thereof.

In some embodiments, one or more of the following may include at least one accessory attachment member: the side support member(s) (e.g., one or more of the legs); support arm(s); support member(s); transverse member; or a combination thereof. Each of these may include the same or different combination of accessory attachment members. For example, each of these may include the same or different accessory attachment members, as well as the same or different number of attachment members.

In some embodiments, the accessory attachment members may extend from these components of the device. For example, the accessory attachment members may have a wire-like frame. In other embodiments, the accessory attachment members may be disposed within the component(s) of the device. For example, the accessory attachment members may be cut-outs disposed within the component(s) of the device.

In some embodiments, one or both support arm may include at least one accessory attachment member. In some embodiments, the support arm may include one attachment member disposed along at least its portion of its length. In other embodiments, the support arm may include more than one disposed along its length. Although the figures show that each arm has three accessory attachment members, it will be understood that the device may include more or less accessory attachment members. Additionally, the accessory attachment members may have a different configuration (e.g., an elongated open hook with a planar surface), as well as a different combination of accessory attachment members.

As shown in FIGS. 1 through 3, the support arms 160 and 170 may include at least one accessory attachment members 162 and 172, respectively. In some embodiments, one or more of the support arms may include a plurality of accessory attachment members. In some embodiments, the support arms 160 and 170 may include at least three accessory attachment members. The support arms 160 and 170 may include a first accessory attachment member 162,172; a second accessory attachment member 164,174; and a third accessory attachment member 166,176, respectively. In other embodiments, the support arms 160 and 170 may include more or less accessory attachment members.

Additionally, the transverse member may include an accessory attachment member. The accessory attachment member may protrude from the transverse member at an angle so as to be also configured to provide support for the drape. The accessory attachment member may extend substantially along the length of the transverse member. As shown in FIGS. 1-3, the transverse member 132 may include accessory attachment member 136.

In some embodiments, one or both side supports may include at least one accessory attachment member. As mentioned above, the side supports may include openings, for example, disposed within a leg. These openings may be configured to be accessory attachment members.

Additionally, in some embodiments, one or both support members may include at least one accessory attachment member. For example, the device may include an accessory attachment member extending from one or both support members. FIGS. 5-8 show an example of a device 500 that includes an accessory attachment member 512 and 514 extending from support members 502 and 504, respectively.

The components of the surgical support device 100 may be made of any light-weight material capable of being easily sterilized. The components may be made of the same material, different materials, or a combination thereof. The materials may include but is not limited to stainless steel, aluminum or any of various other suitable metals, alloys, polymers, or composite materials.

In some embodiments, one or more components of the surgical support device 100 may include guides to help reduce wear. For example, the guide may include but is not limited to a Teflon guide. The one or more components may include but is not limited to pivoting mechanisms 152 and 154 and support arms 160 and 170.

Figure 4:
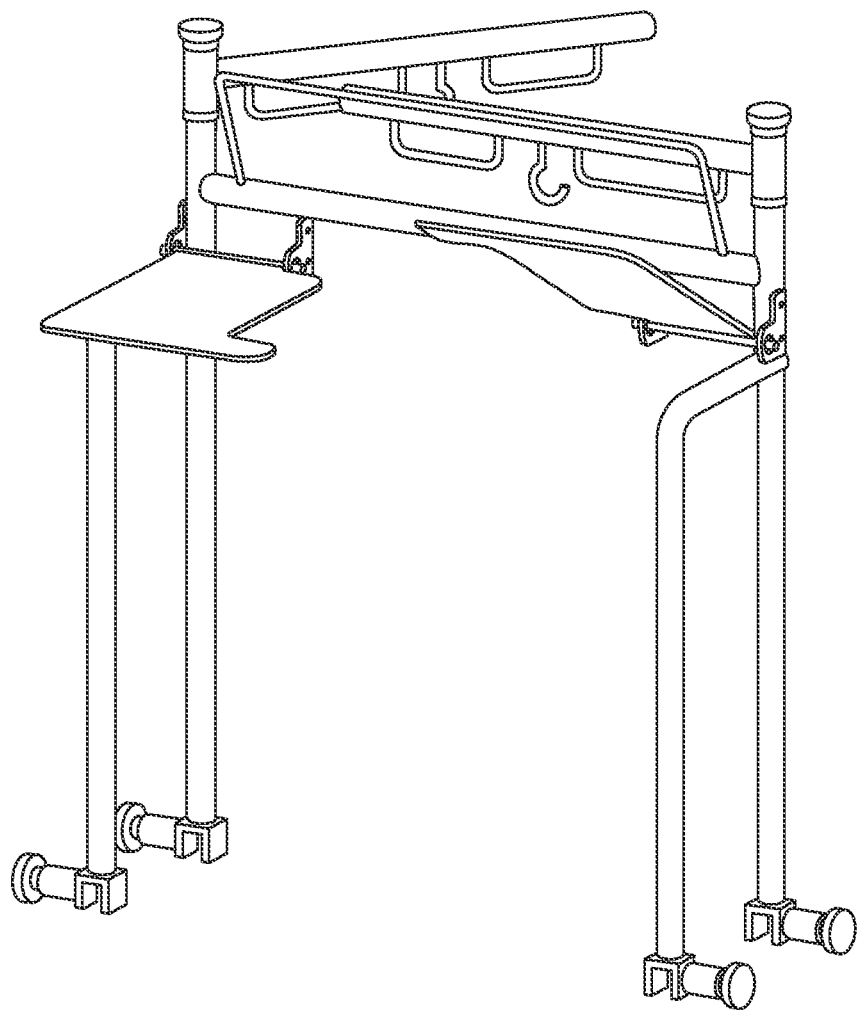
FIG. 4 is another perspective view of a surgical support device according to embodiments.

FIG. 4 shows a computer-rendered version of the device 100. FIGS. 5-8 show different views of device 500, which is an example of a prototype of the device 100.

As shown in FIGS. 5-8, the surgical support device 100 may be configured to be collapsible. In some embodiments, the device may additionally and/or alternatively be configured to be disposed in a collapsed position or state. In some embodiments, the support arms may be configured to be disposed in a collapsed position. For example, FIGS. 5-8, show the arm supports in different states or positions of expansion and collapse. In the collapsed state or position, the arm supports are configured to be disposed parallel to the transverse member. In some embodiments, the arm supports may be configured to be disposed behind and substantially adjacent to the accessory attachment member of the transverse member. In the open state or position, the arm supports are configured to extend outwardly from the side support.

In some embodiments, as shown in FIG. 5, at least one of support platforms may be configured to be disposed in a collapsed position so as to be substantially adjacent to the transverse member. In some embodiments, the support platforms may be configured to be disposed substantially abut to the transverse member in the collapsed position. In the open position, the support platforms may be disposed above and/or abut the support member.

Although not shown, in some embodiments, at least one side support may be configured to be disposed in a collapsed position so as to be substantially adjacent to the transverse member. In some embodiments, the at least one side support may be configured to be disposed substantially parallel to the transverse member in the collapsed position. The figures show the side supports in an open or expanded position.

In this way, the device, in a collapsed position, may be disposed in single plane (e.g., the arm supports and/or support arms are disposed adjacent to the transverse member) and thereby can be easily stored.

While the disclosure has been described in detail with reference to exemplary embodiments, those skilled in the art will appreciate that various modifications and substitutions can be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. A surgical support device configured to be disposed on side rails of a surgical table, comprising:
   at least two side supports configured to extend vertically from and fixedly dispose to the side rails, each side support including a support member extending perpendicular to a length of the each side support;
   a transverse member disposed between and connects to the side supports;
   at least one platform configured to be pivotable between a first substantially vertical position and a second substantially horizontal position, the at least one platform substantially abutting the transverse member in the first position and the at least one platform substantially abutting at least one of the support members in the second position;
   a pivoting mechanism fixedly disposed between the transverse member and the at least one of the support members and connected to the at least one platform, the pivoting mechanism being configured to pivot the at least one platform between the first position and the second position; and
   at least one accessory attachment member configured to secure and/or support one or more accessories.

2. The device of claim 1, further comprising:
   at least two connectors, each connector disposed at an end of each side support and configured to at least partially surround a side rail and fixedly dispose the device to the surgical table.

3. The device of claim 1, further comprising:
at least one accessory arm extending from at least one of the side supports and configured to pivot around the at least one of the side supports; and
a locking mechanism configured to releasably lock the at least one accessory arm in position.

4. The device of claim 1, further comprising:
at least one accessory arm extending from at least one of the side supports and configured to pivot around the at least one of the side supports;
wherein the at least one accessory arm includes the at least one accessory attachment member.

5. The device of claim 1, wherein one or more of the following includes the at least one accessory attachment member: an accessory arm, at least one of the side supports, the transverse member, and at least one of the support members.

6. The device of claim 1, wherein:
the device is configured to move between an expanded position and a collapsed position;
the side supports are configured to move between the expanded position and the collapsed position;
the side supports are disposed substantially perpendicular to the transverse member in the expanded position; and
the side supports are disposed substantially parallel to the transverse member in the collapsed position.

7. The device of claim 1, wherein:
each side support includes two legs, one of the legs of each side support being longer than another leg of the each side support; and
each support member extending between the two legs.

8. The device of claim 1,
wherein the at least one platform includes a cut-out portion.

9. The device of claim 1, wherein at least one of the side supports includes an opening.

10. The device of claim 9, wherein each side support includes two legs.

11. The device of claim 1, further comprising:
a securing member configured to maintain the platform in the first position or the second position.

12. A surgical support device configured to be disposed on side rails of a surgical table, comprising:
at least two side supports configured to extend vertically from and fixedly dispose to the side rails, each side support including a set of legs and a support member disposed perpendicular to and between each set of legs;
a transverse member disposed between and connects to the side supports;
at least one platform configured to be pivotable between the transverse member and at least one of the support members, the at least one platform substantially abutting the transverse member in a first substantially vertical position and the at least one platform substantially abutting the at least one of the support members in a second substantially horizontal position;
a pivoting mechanism fixedly disposed between the transverse member and the at least one of the support members and connected to the at least one platform, the pivoting mechanism being configured to pivot the at least one platform between the first position and the second position;
at least one accessory arm extending from the at least one of the side supports and configured to pivot around one of the side supports; and
a plurality of accessory attachment members configured to secure and/or support one or more accessories, the plurality of accessory attachment members being disposed on one or more of the following: the at least one accessory arm, at least one of the at least two side supports, the transverse member, and at least one support member.

13. The device according to claim 12, further comprising:
a locking mechanism configured to releasably lock the at least one accessory arm in position.

14. The device of claim 12, wherein:
the device is configured to move between an expanded position and a collapsed position; and
in the collapsed position, the side supports, the at least one platform, and/or the at least one accessory arm is disposed substantially parallel to the transverse member.

15. The device of claim 12, wherein the device includes two platforms that are separated by an opening.

16. A surgical support device configured to be disposed on side rails of a surgical table, comprising:
at least two side supports configured to extend vertically from and secure to the side rails, each side support including a support member extending perpendicular to a length of the each side support;
a transverse member disposed between and connected to the side supports;
at least one platform configured to be pivotable between the transverse member and at least one of support members, the at least one platform substantially abutting the transverse member in a first substantially vertical position and the at least one platform substantially abutting the at least one of the support members in a second substantially horizontal position;
a pivoting mechanism fixedly disposed between the transverse member and the at least one of the support members and connected to the at least one platform, the pivoting mechanism being configured to pivot the at least one platform between the first position and the second position;
at least one accessory arm extending from the at least one of the at least two side supports and configured to pivot around one of the at least two side supports; and
a plurality of accessory attachment members configured to secure and/or support one or more accessories;
wherein the at least one accessory arm, at least one of the side supports, the transverse member, and/or at least one of the support members includes at least one of the accessory attachment members;
wherein the device is configured to move between an expanded position and a collapsed position; and
wherein in the collapsed position, the side supports, the at least one platform, and/or the at least one accessory arm is disposed substantially parallel to the transverse member.

17. The device according to claim 16, further comprising:
a locking mechanism configured to releasably lock the at least one accessory arm in position.

18. The device of claim 16, wherein the device includes two platforms that are separated by an opening.

19. The device of claim 16, wherein at least one of the side supports includes an opening.

* * * * *